(12) United States Patent
Cassidy

(10) Patent No.: US 7,547,295 B2
(45) Date of Patent: Jun. 16, 2009

(54) GAS REMOVAL IN AN INTRAVENOUS FLUID DELIVERY SYSTEM

(75) Inventor: David E. Cassidy, Chelmsford, MA (US)

(73) Assignee: Enginivity, LLC, Lexington, MA (US)

( * ) Notice: Subject to any disclaimer, the term of this patent is extended or adjusted under 35 U.S.C. 154(b) by 130 days.

(21) Appl. No.: 11/140,087

(22) Filed: May 27, 2005

(65) Prior Publication Data
US 2006/0025725 A1    Feb. 2, 2006

Related U.S. Application Data

(60) Provisional application No. 60/575,246, filed on May 8, 2004, provisional application No. 60/576,258, filed on Jun. 2, 2004.

(51) Int. Cl.
*A61M 35/00* (2006.01)

(52) U.S. Cl. .................. 604/122; 604/123; 604/127; 604/131

(58) Field of Classification Search .................. 604/251, 604/80, 246, 247, 255, 256, 257, 260, 122, 604/123, 127, 131
See application file for complete search history.

(56) References Cited

U.S. PATENT DOCUMENTS

| | | | |
|---|---|---|---|
| 4,191,184 A | 3/1980 | Carlisle | 128/214 |
| 4,273,121 A * | 6/1981 | Jassawalla | 604/153 |
| 4,457,750 A | 7/1984 | Hill | 604/65 |
| 4,504,263 A | 3/1985 | Steuer et al. | 604/65 |
| 4,525,163 A * | 6/1985 | Slavik et al. | 604/65 |
| 4,613,325 A | 9/1986 | Abrams | 604/65 |
| 4,645,489 A | 2/1987 | Krumme et al. | 604/65 |
| 4,827,970 A | 5/1989 | Sugisaki et al. | 137/486 |
| 4,938,079 A | 7/1990 | Goldberg | 73/861.95 |
| 5,026,348 A | 6/1991 | Venegas | 604/122 |
| 5,319,170 A | 6/1994 | Cassidy | 219/630 |
| 5,356,378 A | 10/1994 | Doan | 604/65 |
| 5,399,171 A | 3/1995 | Bowman et al. | 604/247 |
| 5,779,674 A * | 7/1998 | Ford | 604/126 |
| 5,807,312 A * | 9/1998 | Dzwonkiewicz | 604/30 |
| 5,865,813 A | 2/1999 | DeKalb et al. | 604/250 |
| 6,480,257 B2 | 11/2002 | Cassidy et al. | 352/470 |

* cited by examiner

*Primary Examiner*—Nicholas D Lucchesi
*Assistant Examiner*—Laura A Bouchelle
(74) *Attorney, Agent, or Firm*—Alan Taboada; Moser IP Law Group

(57) ABSTRACT

An active gas removal system is provided to remove air or gas bubbles from an intravenous fluid prior to infusion into the patient. The system detects the level of liquid in a drip chamber and occludes a downstream valve to the patient, thereby increasing pressure in the drip chamber sufficient to open a vent valve and release gas therein.

11 Claims, 16 Drawing Sheets

Dielectric measurement at full compression

US 7,547,295 B2

GAS REMOVAL IN AN INTRAVENOUS FLUID DELIVERY SYSTEM

CROSS REFERENCE TO RELATED APPLICATIONS

This application claims the benefit under 35 U.S.C. § 119 (e) of U.S. Provisional Patent Application No. 60/575,246, filed May 28, 2004, and U.S. Provisional Patent Application No. 60/576,258, filed Jun. 2, 2004, the disclosures of both of which are incorporated by reference herein.

This application is related to commonly owned U.S. patent applications entitled Flow Control in an Intravenous Fluid Delivery System, filed concurrently herewith, and Gas Detection in an Intravenous Fluid Delivery System, filed concurrently herewith.

STATEMENT REGARDING FEDERALLY SPONSORED RESEARCH OR DEVELOPMENT

N/A

BACKGROUND OF THE INVENTION

Devices to deliver fluids intravenously to a patient involve a number of considerations, such as air or gas bubble detection, gas removal, and flow rate control.

Air and bubble detection in medical intravenous (IV) fluid delivery systems is important. Large amounts of air can cause air embolisms in any part of the body, blocking off blood flow. Embolisms in the brain can cause severe memory loss and even death. Air trapped in the heart can also cause death or heart damage. Ultrasonic, optical, and electrical conductivity methods are used in the prior art detection of air bubbles in medical IV fluid lines.

Ultrasonic detectors are the most widely used detectors in the IV medical fluid delivery field and are based on the fact that sound is more readily conductive through liquid than through air. Thus, an air bubble does not "conduct" sound from one side of the tubing wall to the other, while fluid does conduct sound. Ultrasonic detectors are effective at detecting small amounts of gas in IV tubing, but have a number of drawbacks. They are expensive. They require that the tubing be in direct contact with the ultrasonic transmitter and receiver. Moreover, the slightest air gap can trigger the detector, causing a false alarm. Micro bubbles that build up on the surface of the tubing and are too small to be harmful also can trigger false alarms, since the micro bubbles, despite their very small size, still provide a boundary to the ultrasound. In addition, ultrasonic detectors have a fairly high power consumption, greater than 100 mW.

Optical detectors are typically inexpensive. Some optical detectors work using light absorption while others use light transmission. These methods are, however, fluid dependent and therefore not very common, because many different fluids are used for IVs. Also, their performance is dependent on the optical characteristics of the tubing, and many different tubing sets, having different optical characteristics, can be used. Additionally, optical detectors can be subject to interference from light from other sources.

Electrical conductivity detectors are used the least, as they require a direct electrical connection to the IV fluid. To electrically isolate the patient, this connection must have low leakage current and high dielectric strength. Typically, two or three electrodes are placed in contact with the fluid and are excited from an AC or DC source while the current/voltage is monitored. Gas bubbles do not conduct electricity, but many IV fluids do. A drawback, however, is that some IV fluids do not conduct electricity. Another drawback is that a thin film of fluid connecting one electrode to the other where the electrode penetrates the tubing wall can give a false detection of fluid presence.

When a fluid is heated, outgassing occurs. In prior art IV fluid warming devices, outgassing has either been ignored or handled with elaborate schemes. In one scheme, a hydrophobic filter has been employed to vent gases. This system is disadvantageous, because it is difficult and expensive to test to ensure that the filter does not leak. Also, the check valve used to prevent air from entering the system can stick, for example, if the humidity becomes too high or if another fluid inadvertently drips onto the valve, thereby requiring a greater pressure to open the valve. In another scheme, a drip chamber is used to collect the gases. This scheme is disadvantageous, because the chamber has a fixed volume and once full, the air can enter the patient unless a manually operated venting drip chamber is employed. A user must remember to vent such a venting drip chamber.

Intravenous (IV) fluids need to be delivered at different rates. Hydration fluids typically are delivered at higher rates, while drugs are typically delivered at lower rates. Flow rate control in medical IV fluid devices involves considerations of flow rate accuracy, errors made by personnel in setting flow rates, cost, and set up time. Three main types of devices are used in the control of IV fluid flow rates, namely, roller clamps, volumetric pumps, either volume displacement pumps or valve-regulated gravity assist pumps, and in line mechanical flow regulators.

Roller clamps are the most widely used flow control device. The roller clamp comprises a wheel trapped within a housing that compresses the IV tubing as it is slid along a gradual ramp. The flow rate is calculated by counting drips in a drip chamber. This device is inexpensive, but has a number of drawbacks. The setup operator must take time to count drips into the drip chamber, an iterative process taking up to 15 seconds for each adjustment. Also, the setup operator must know the size of the drips and must calculate the flow rate and may make a mistake. Even after it is set up, the IV tubing in the clamp continues to deform over time, causing the rate to change. The IV solution must be held above the patient insertion site. Any changes in height can affect the flow rate, because the roller clamp is a relative device. The advantages of the roller clamp are that it does not require any power, it is widely accepted, and it is inexpensive.

Volumetric pumps are also widely used for drug delivery. There are two main types of infusion rate control. In a first type of control, a displacement pump forces fluid through the IV line at repeatable volumes and adjustable intervals. These pumps can be reciprocating piston, peristaltic (linear or rotary), or syringe types. These pumps are typically quite precise, as required for drug delivery, and are not typically used for standard IVs. A second type of infusion rate control utilizes gravity driven fluid. With this type, drips through a drip chamber are counted, and a variable orifice valve is controlled based upon the number of drips over time.

A disadvantage of such pumps is their great expense. Also, the tubing set is typically disposable, which further increases the cost. These pumps also take up a lot of space. The main advantages of such pumps are accurate flow control, no change in flow with change in bag height, reduced setup time, and reduced chance of error by the operator.

In line mechanical flow regulators, using diaphragms, needles valves, and the like, are not very common. They are advantageous in that they require no power and are reasonably independent of IV fluid bag height. They are, however, dependent on fluid viscosity. Also, they typically have two flow rate scales (ml/min and ml/hour), which, while providing versatility, can also be confused by operating personnel.

SUMMARY OF THE INVENTION

In one aspect of the present invention, an air or gas bubble detection system is provided that detects the presence or absence of liquid in intravenous (IV) tubing. By detecting the presence of liquid rather than gas, false alarms due to micro bubbles or small air gaps between the sensor and the tubing are avoided. This system is independent of fluid type. Additionally, high electrical isolation is maintained and leakage currents are acceptably low. Also, power consumption is low with the present system.

More particularly, the air or gas bubble detection system employs a circuit that transfers a charge to a sense electrode adjacent the IV tubing and to a reference capacitor. Two grounded electrodes are spaced on the sides of the sense electrode. The three electrodes are aligned parallel with the length of the IV tubing. The tubing and any fluid (liquid or gas) therein act as dielectrics. A grounded shield electrode shapes the electric field toward the tubing and prevents outside fields from interfering with the sensing process. The circuit detects the amount of charge transferred to the reference capacitor, which is indicative of the type of material present. The presence of a liquid produces a high number, whereas the absence of a liquid produces a low number. By comparing the produced number with a limit, the controller determines if an alarm condition is met.

In another aspect of the present invention, an active gas removal system is provided to remove air or gas bubbles from an intravenous fluid prior to infusion into the patient. The gas removal system employs a drip chamber through which intravenous fluid is pumped by an upstream pump. The IV fluid exits the chamber through an outlet in the bottom, while gas or air is retained in the upper portion of the chamber. A vent valve at the top of the drip chamber is operative to open upon an increase of gas pressure within the drip chamber to vent the gas in the chamber. A controller is provided in communication with a fluid level sensor in the drip chamber and with a downstream patient line-occluding valve. The controller is operative to close the downstream valve upon detection of a specified fluid level in the drip chamber detected by the fluid level sensor, whereby a pressure increase in the drip chamber caused by continued operation of the upstream pump opens the vent valve and releases gas retained within the drip chamber.

A further aspect of the present invention relates to an intravenous (IV) flow control system that employs tubing orifice size data and thermal data from a fluid warming system to provide closed loop control to maintain a desired flow rate. The actual flow rate is determined by two techniques, a geometrically based technique that uses geometric parameters of the IV tubing system, and a thermally based technique that uses the power input to an IV fluid warmer and the temperature of the IV fluid entering and exiting the warmer.

The system employs a pincer or other moveable element positioned to compress the tubing, forming an orifice at which flow can be controlled. The geometry of the tubing at the orifice can be determined by a force transducer, the data from which is fed to a system controller that calculates flow rate based on orifice geometry data. The thermal data from the fluid warmer is also fed to the controller, which calculates flow rate from this data also. Based on the combined calculations of the orifice geometry and the thermal transfer data, the pincer is controlled to adjust the flow at the orifice to maintain the desired flow rate.

The system is advantageous, because it can utilize a standard hospital IV set and standard hospital procedure. It can adapt to real time changes in the tubing, and it can handle both standard IV fluids and blood. The system utilizes two independent control loops to calculate and control flow rate, and can switch to one or the other control loop to suit circumstances. For example, at higher flow rates, the thermally based control loop is usually preferred. The system can also be operated to allow infusion of a bolus of fluid to the patient.

DESCRIPTION OF THE DRAWINGS

The invention will be more fully understood from the following detailed description taken in conjunction with the accompanying drawings in which.

DETAILED DESCRIPTION OF THE INVENTION

Gas Bubble Detection System

The present invention relates in one aspect to an air or gas bubble detection system for use with an intravenous (IV) fluid infusion system. The system of the present invention detects the presence or absence of liquid in the IV tubing, not the presence of gas. If the system detects that liquid is not present, then gas must be present in the tubing. With this system, false alarms due to detection of micro bubbles or small air gaps between the sensor and the tubing are avoided.

More particularly, all materials have a physical dielectric constant. Gasses have a very low dielectric constant, plastics have a medium dielectric constant, and liquids have a very high dielectric constant. The present system utilizes electrodes to act as capacitor plates and the adjacent materials (the tubing and any fluid therein) as dielectrics. The detected charge on a reference capacitor is indicative of the type of material present.

Figure 1:
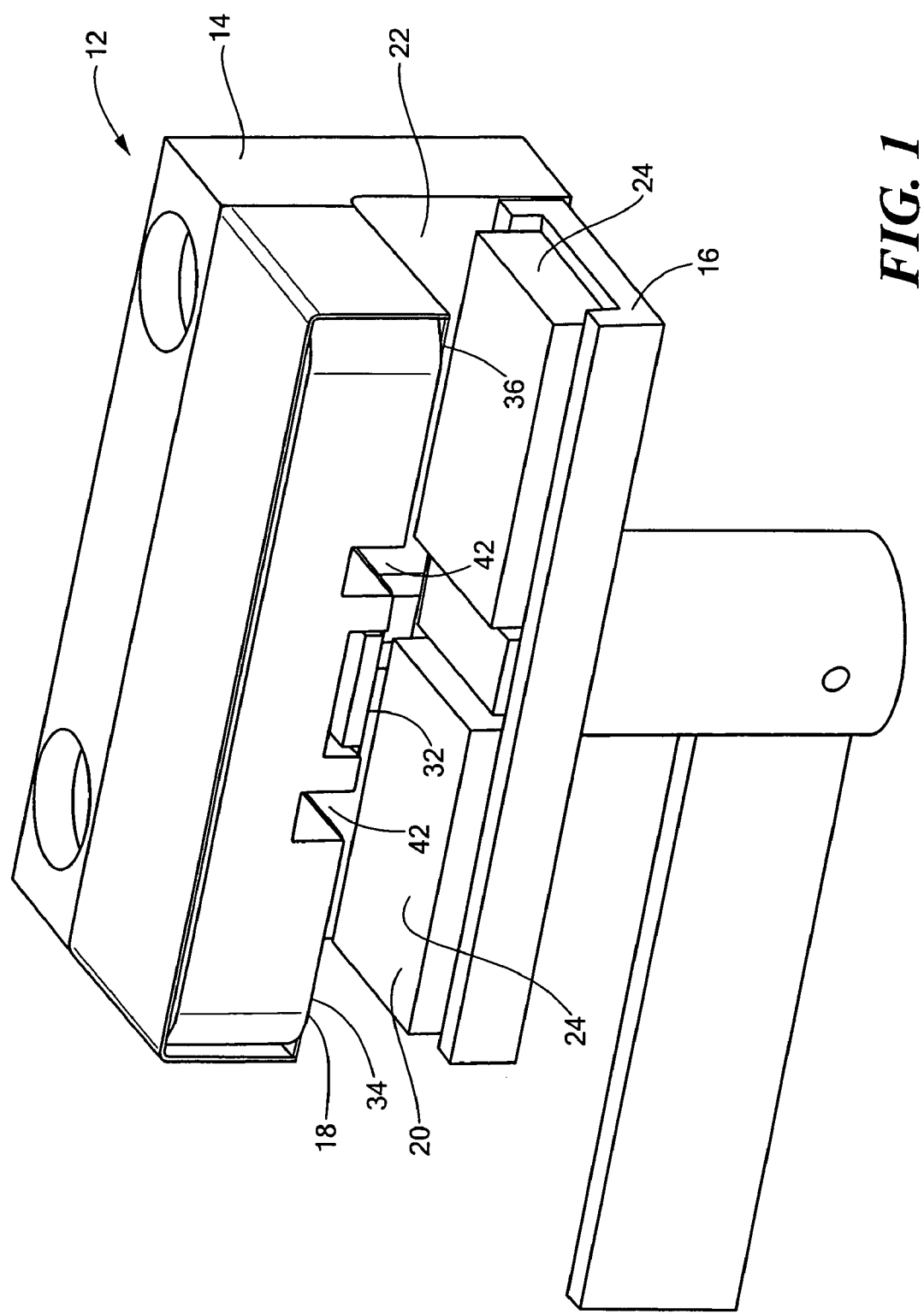
FIG. 1 is an isometric view of an air or gas bubble detection system of the present invention for an intravenous (IV) infusion system.
Figure 2:
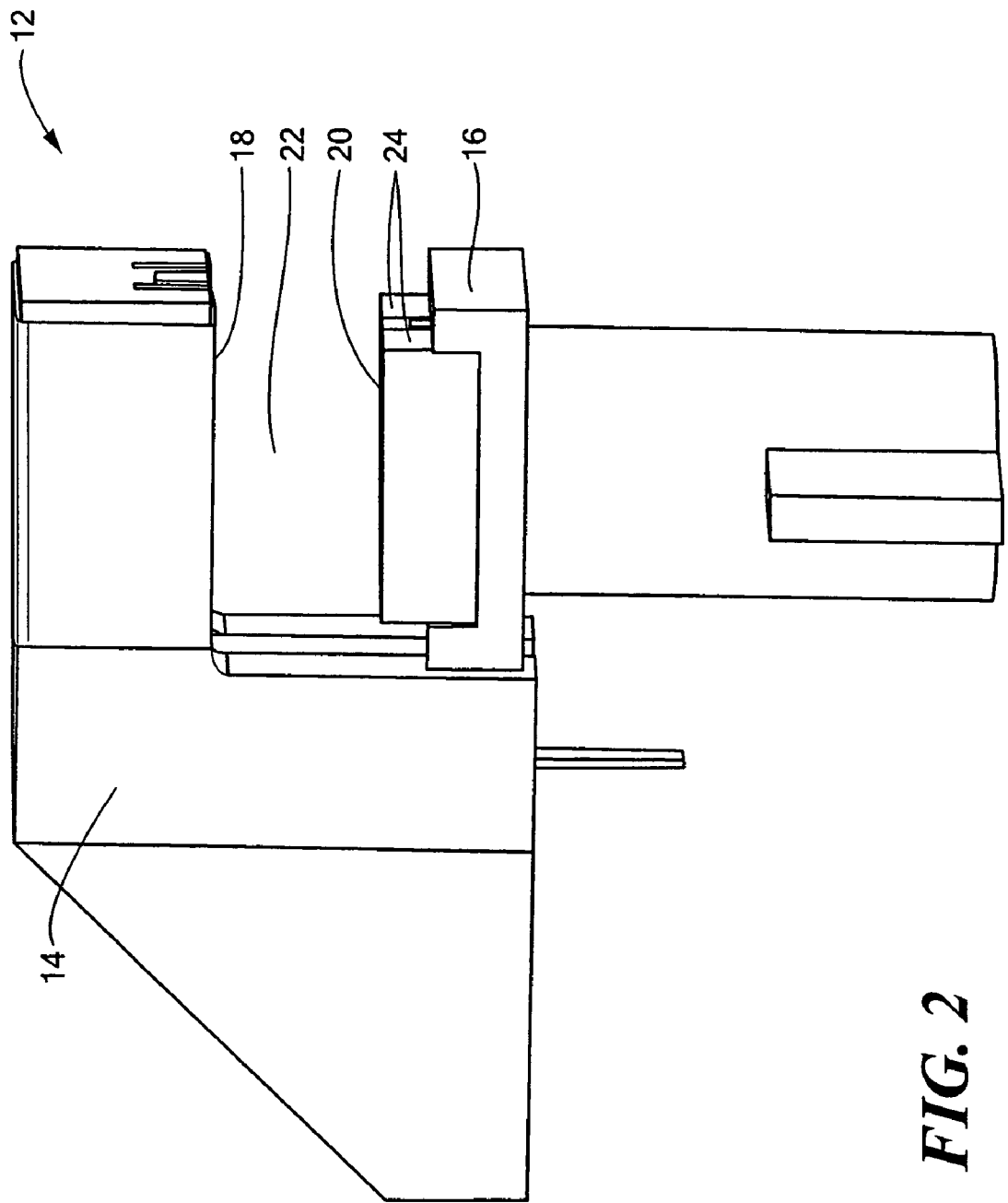
FIG. 2 is an isometric side view of the air or gas bubble detection system of FIG. 1.
Figure 3:
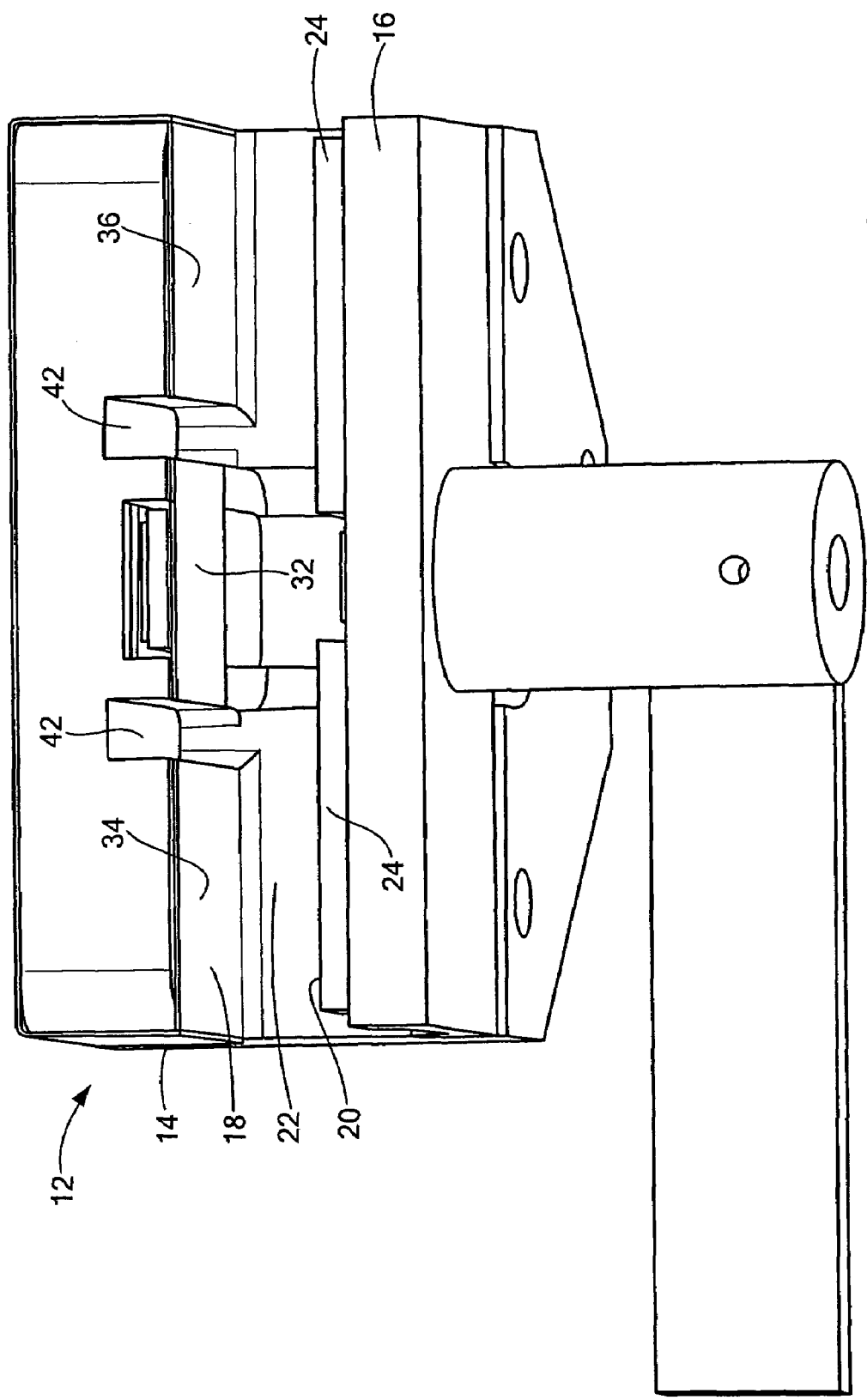
FIG. 3 is an isometric bottom view of the air or gas bubble detection system of FIG. 1.

Referring to FIGS. 1-3, the system employs a body or housing 12 having a support member 14, generally L-shaped in cross-section in the embodiment illustrated, and a holding member 16. The support member and the holding member provide generally opposed faces 18, 20 that define a channel 22 or other suitable recess configured to receive a portion of the IV tubing.

Figure 4:
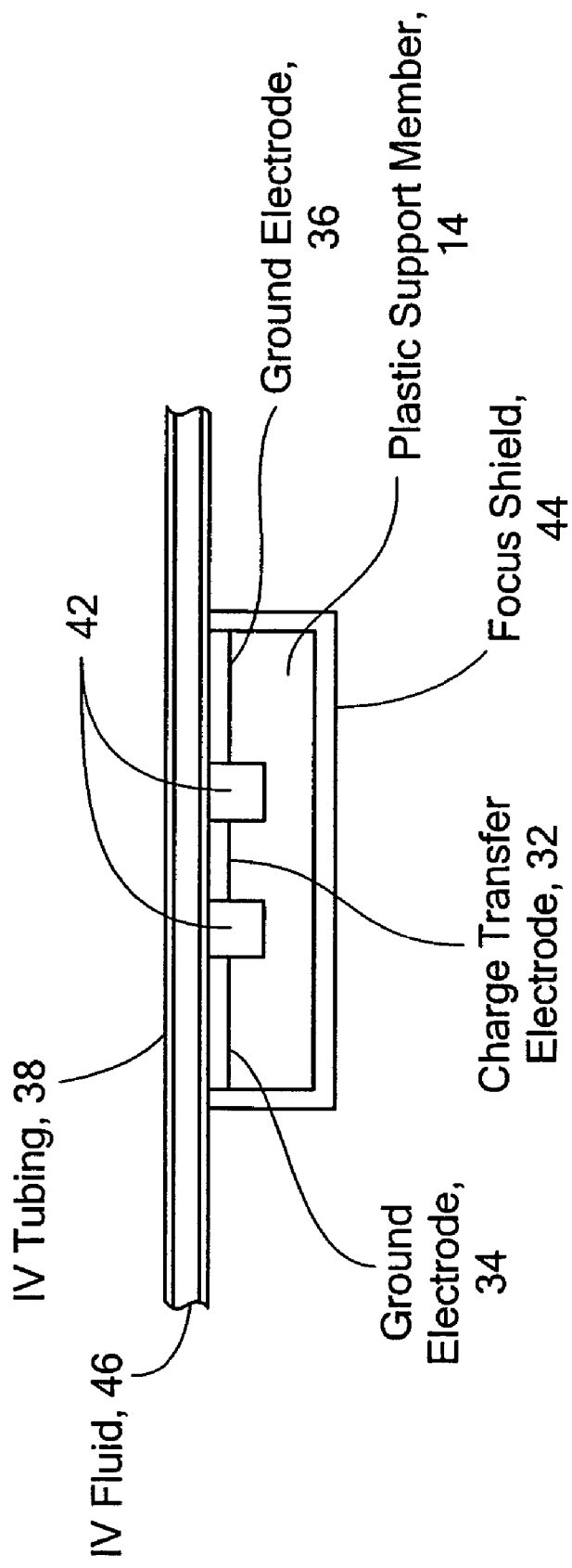
FIG. 4 is a schematic view of the air or gas bubble detection system of FIG. 1.

Referring also to FIG. 4, the support member 14 is made of a suitable insulating material, such as a plastic. Three electrodes 32, 34, 36 are mounted on the support member in series relative to each other and parallel with the portion of the IV tubing 38 held in the channel. In this manner, the three electrodes form the channel face 18 of the support member that contacts the tubing.

The tubing must be held in contact with the three electrodes. Toward this end, the channel may be sized to provide a snug fit for the tubing, or the holding member may be configured to apply a clamping force to the tubing portion, such as with a movable element or piston, to ensure the tubing portion is retained in the body. The holding member may include pads 24 (FIGS. 1-3), such as of foam rubber, to hold the tubing in contact with the opposed face of the support member and prevent the tubing from shifting or otherwise moving.

Figure 5:
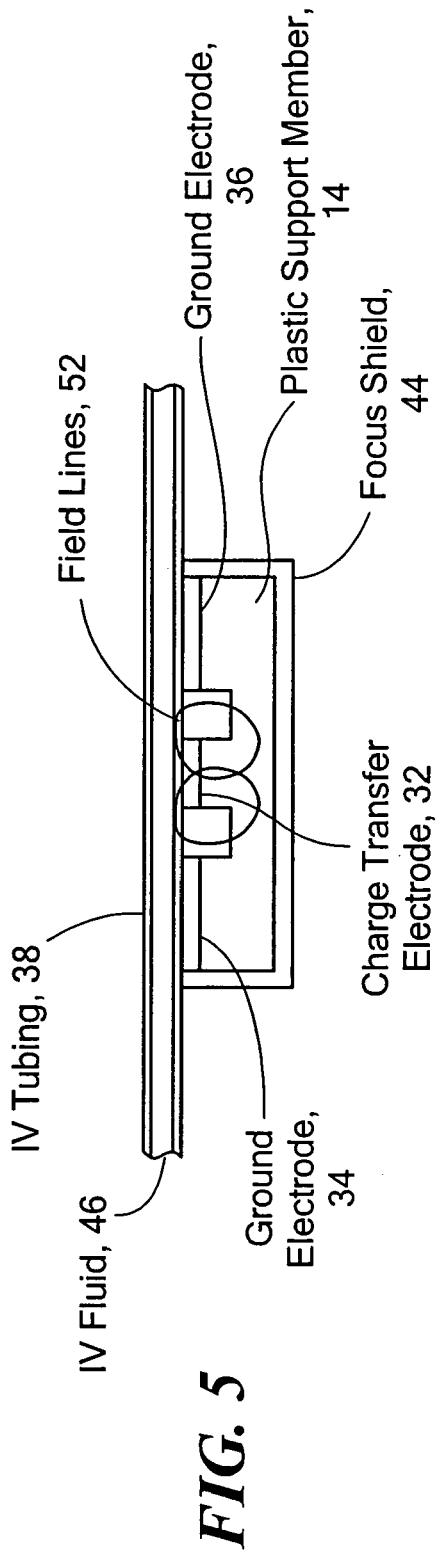
FIG. 5 is a schematic view of the air or gas bubble detection system of FIG. 1 illustrating field lines when fluid is present in the tubing.
Figure 6:
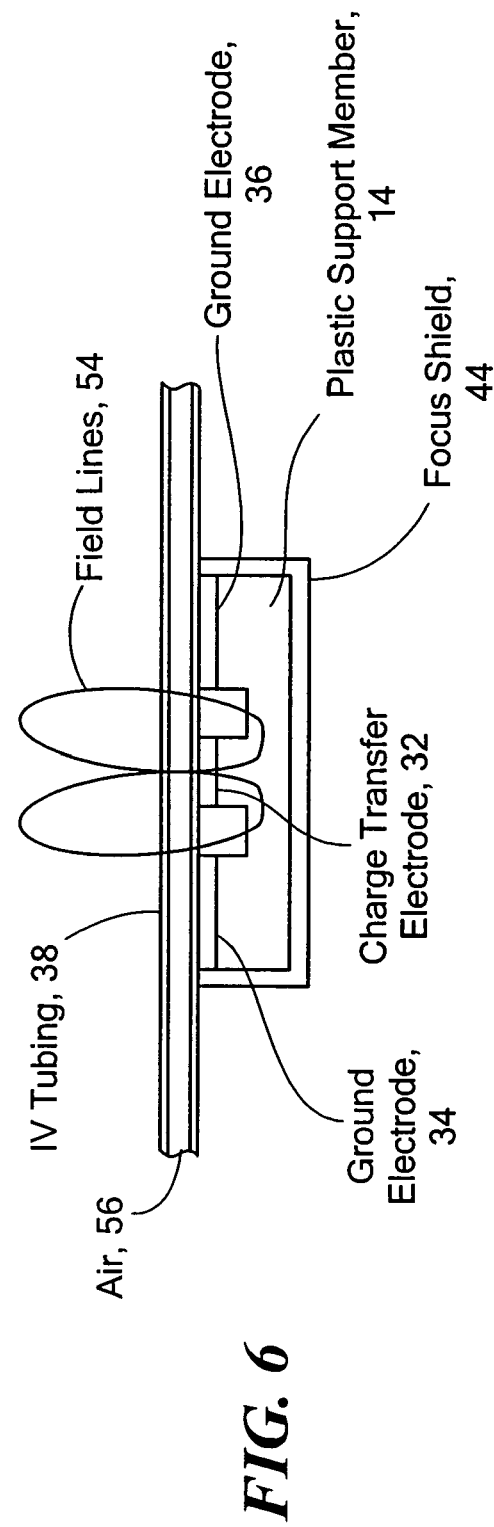
FIG. 6 is a schematic view of the air or gas bubble detection system of FIG. 1 illustrating field lines when air is present in the tubing.

The two outer electrodes 34, 36 are grounded. The middle sense or charge transfer electrode 32 is used to transfer a charge of electrons to its surroundings. Two air gaps or spaces 42 are formed in the support member on each side of the sense electrode 32 to limit coupling fields from the sense electrode to the ground electrodes. The electrodes are arranged in such a way that the electric field is focused toward and over a short section of the IV tubing. The ground electrodes 34, 36 at opposite ends of the detector establish the length of tubing being tested, that is, the length of the sense electrode 32 along the tubing plus the air gaps 42. As noted above, the electrodes act as capacitor plates and the adjacent materials (the tubing and any fluid therein) act as dielectrics. A fourth shield electrode 44 is provided around the support member 16 of the body. The shield electrode is grounded and shapes or directs the electric field toward the tubing. The shield electrode also keeps extraneous outside fields from interfering with the sensing process. FIG. 5 illustrates electric field lines 52 when a liquid 46 is present in the tubing, but no gas is present in the tubing. FIG. 6 illustrates electric field lines 54 when air 56 is present in the tubing.

Figure 7:
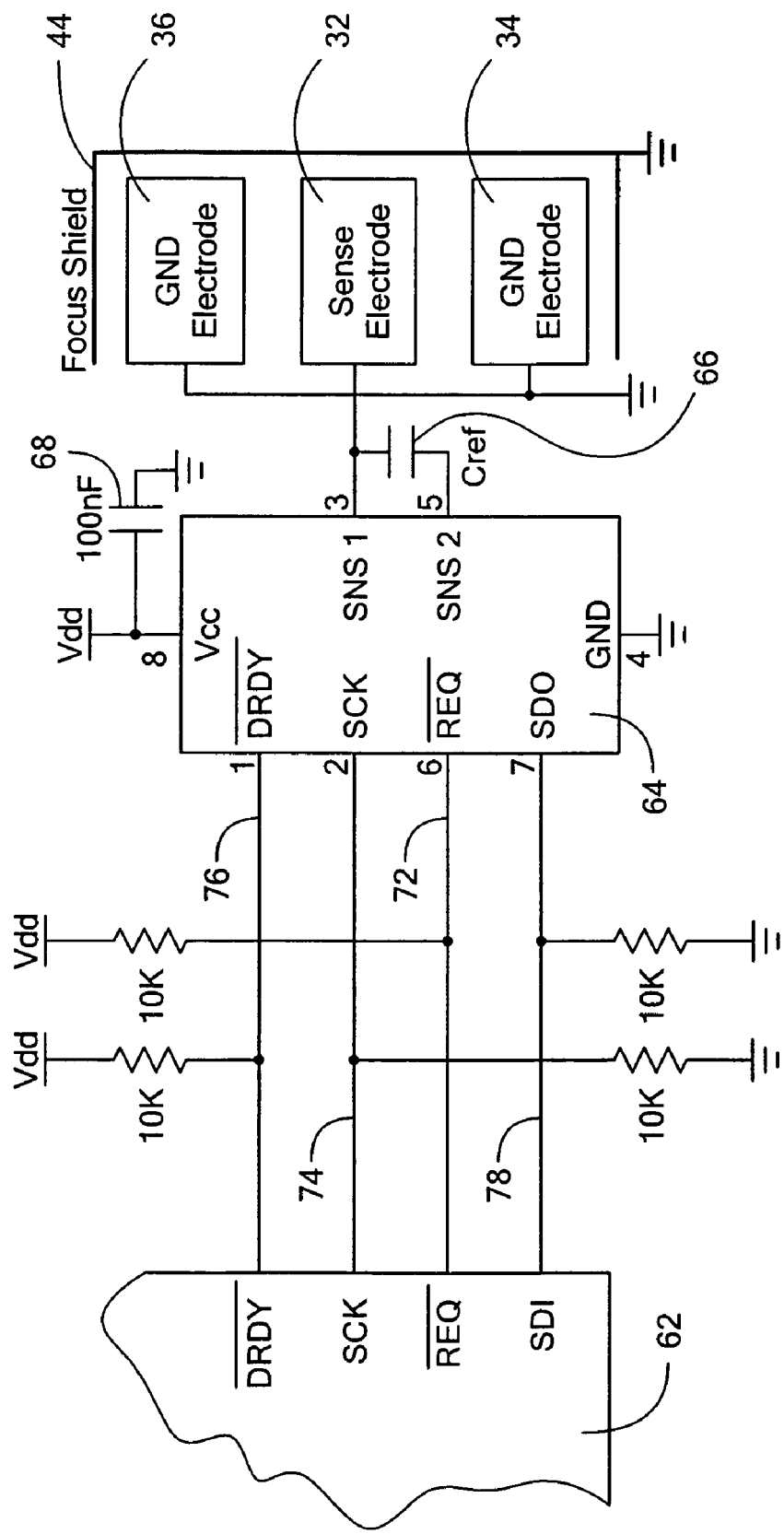
FIG. 7 is an electrical schematic of a circuit operative to detect capacitance of the tubing and fluid for the air or gas bubble detection system of FIG. 1.

Referring to FIG. 7, a controller or microprocessor 62 is in communication with a charge transfer device 64, such as a capacitance-to-digital converter integrated circuit (IC). Upon request from the controller, a charge or burst of electrons is placed on the charge transfer electrode 32 and on a reference capacitor 66. The charge transfer device measures the amount of charge transferred to the reference capacitor and converts this charge to a digital number, which is transmitted back to the controller. In the embodiment illustrated, the controller and the charge transfer device are in communication via a line 72 to transmit a signal from the controller to the device to request a burst or charge transfer, a line 74 to transmit clock signals, a data ready line 76 indicating the device is ready to transfer a charge, and a data return line 78 to return data from the device to the controller.

The digitized signal returned to the controller is a ratio of the reference capacitor to the "load capacitance," i.e., the tubing, surrounding plastic, and any fluid (gas or liquid) present in the tubing. The presence of a liquid produces a high number, while the absence of a liquid produces a low number. The controller compares the numbers to limits and determines if an alarm condition is met.

A suitable charge transfer device 64 to be utilized as a capacitance-to-digital converter is the integrated circuit (IC) identified by model QT300, available from Quantum Research Group. The reference capacitor 66 can be any suitable type, such as a plastic film or ceramic capacitor. A bypass capacitor 68 is placed between Vdd and ground for proper operation of the power supply.

The system can be configured so that the operator, such as a physician, can set the bubble size or volume limit. For example, a lesser limit can be set if the patient is a child, and a greater limit can be set if the patient is an adult. For example, a gas volume of 0.5 ml or less may be acceptable in a particular situation. Thus, the system can be set so that only a detected gas volume larger than 0.5 ml triggers an alarm.

Preferably, when an alarm is triggered indicating detection of an air bubble, the IV flow is stopped in any suitable manner. For example, the system can be configured such that the tubing is compressed to occlude completely if the alarm is triggered, preventing further infusion to the patient until the system can be checked by an operator. The system can be used in conjunction with any valve to occlude the tubing. For example, the valve could be located at a pump, at a fluid warmer, or at a gas removal system. The system can be used in conjunction with the IV flow control system of the present invention, described below.

With the present system, the charge transfer method is independent of fluid type. Air gaps do not cause false alarms. Fluid films in the tubing do not cause false alarms. High electrical isolation is maintained. Very low leakage currents are present. Power consumption is very low.

The controller 62 can control the frequency of the burst of electrons to the sense electrode 32 by the charge transfer device 64. Burst control allows for gas volume measurement when the IV flow rate is known. Thus, if the flow rate were low, bursts can be less frequent to detect a particular volume of air than if the flow rate were higher. Similarly, different tubing geometries allow for different size bubbles or volumes to be detected. Thus, if the tubing has a larger diameter, the burst rate can be more frequent to detect the same volume of air than if the tubing had a smaller diameter. The fluid flow rate through the tubing may be known or can be determined in any suitable manner, for example, from a flow rate controller such as that described below. The bubble detection system may be employed with the flow control system described below, or with any other suitable flow control system known in the art.

Gas Removal System

Figure 8:
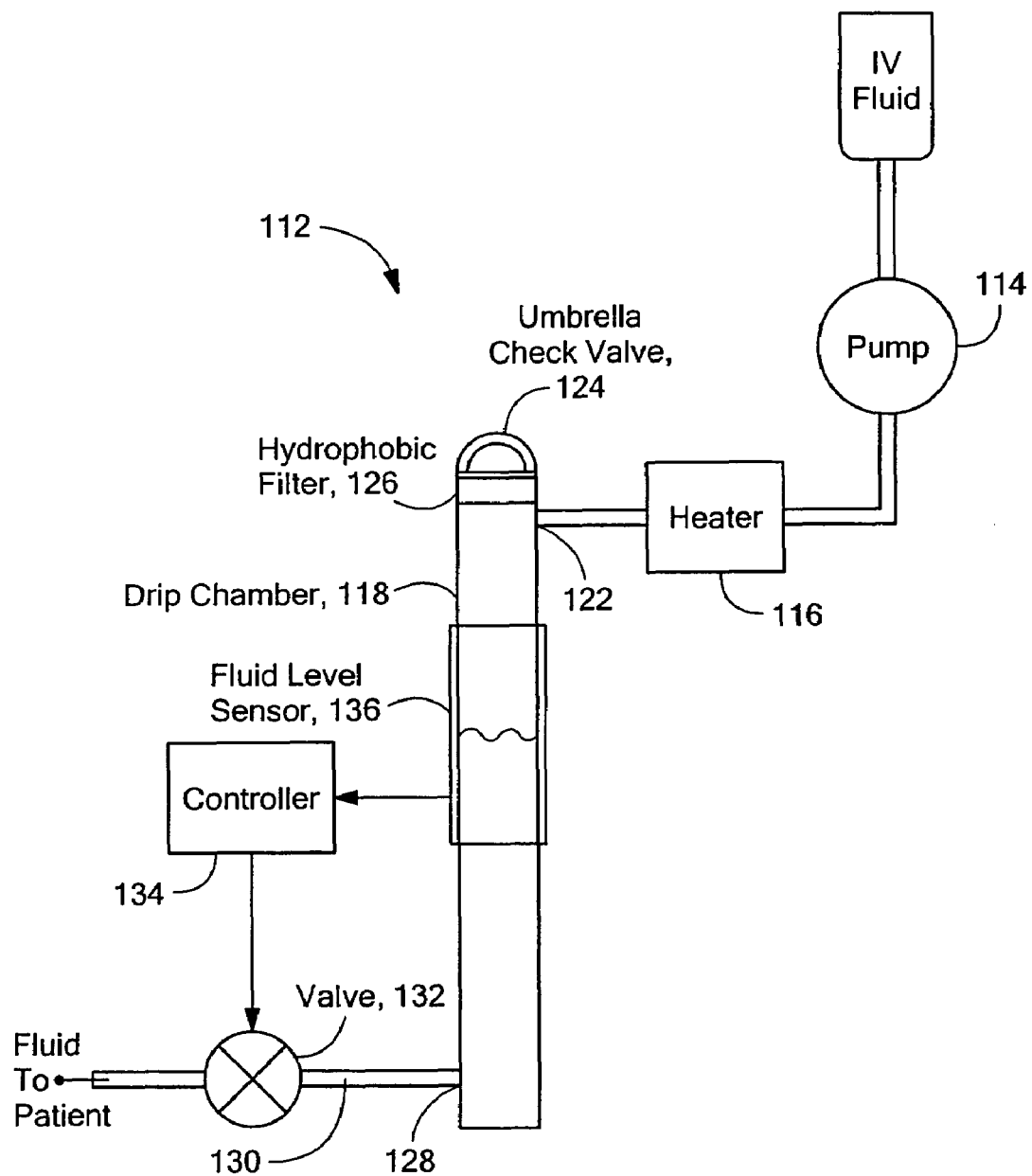
FIG. 8 is a schematic diagram of an air or gas bubble removal system of the present invention.

The present invention also provides an active air or gas removal system, illustrated in FIG. 8. The gas removal system 112 is located downstream from an IV fluid pump 114 and, in the embodiment illustrated, downstream from an IV fluid heater 116. The system includes a drip chamber 118 that receives IV fluid through an input port 122 near the upper end of the chamber 118. A vent valve 124, such as an umbrella or other type of check valve, is located at the top of the drip chamber. When pressure in the chamber is increased (as described further below), the vent valve opens to allow gas to escape from the drip chamber. The vent valve also prevents outside gas from entering the drip chamber. A hydrophobic filter 126 in front of the vent valve prevents the IV fluid from passing through the vent valve.

The IV fluid collected in the drip chamber 118 is introduced to the patient through an output port 128 near the bottom of the chamber via tubing 130 that delivers fluid to the patient. A line-occluding valve 132 in the patient line downstream from the drip chamber is operative to close or reduce flow of fluid therein. Pressure to open the vent valve is generated by occluding the patient line via the downstream line-occluding valve while continuing to run the upstream pump. The pump forces any gas in the drip chamber to be expelled up through the hydrophobic filter and through the vent valve.

A controller 134 is in communication with the patient line valve 132 and with a fluid level sensor 136 that detects the fluid level in the drip chamber 118. Any suitable fluid level detector, such as a float sensor or an ultrasonic detector, can be used, as would be apparent to those of skill in the art. The controller is operative to cause the patient line-occluding valve 132 to close upon detection of a determined low fluid level by the fluid level sensor in the drip chamber, thereby causing pressure to increase in the drip chamber to open the vent valve and preventing gas from traveling to the patient.

The hydrophobic filter does not function when contacted by blood. Thus, the system can include a variable level fluid sensor or multiple fluid level sensors to detect both a low fluid level for purging gas and a high fluid level for preventing contact with the hydrophobic filter. The controller can be operative upon detection of a high level to signal an alarm or take other appropriate action to indicate that the fluid level is too high.

Outgassing occurs when a fluid is heated. Henry's Law can be used to calculate the amount of gas dissolved in a solution versus pressure and temperature, as is known in the art. For example, approximately 7 cc of gas comes out of solution per one liter of fluid at room temperature. Using Henry's Law, it can be determined that a suitable size for the drip chamber is, for example, 50 cc. Other sizes can, of course, be provided, as determined by the application.

The air or gas bubble removal system of the present invention can be employed in conjunction with the system for the detection of air or gas bubbles described above, with any other air or gas bubble detection system, or with any other infusion system.

Intravenous Flow Control System

The present invention also relates to an intravenous (IV) flow control system. The IV flow control system works with a standard hospital IV set and gravity feed and employs a control valve with tubing measurement capabilities and thermal data from a fluid warming system to provide closed loop control to maintain a desired flow rate. More particularly, actual flow rate is determined by two independent control loops to calculate and control the fluid flow rate. One control loop is geometrically based and uses geometric parameters of the IV system. The other control loop is thermally based and uses the power input to an IV fluid warmer and temperatures of the IV fluid entering and exiting the warmer.

Figure 9:
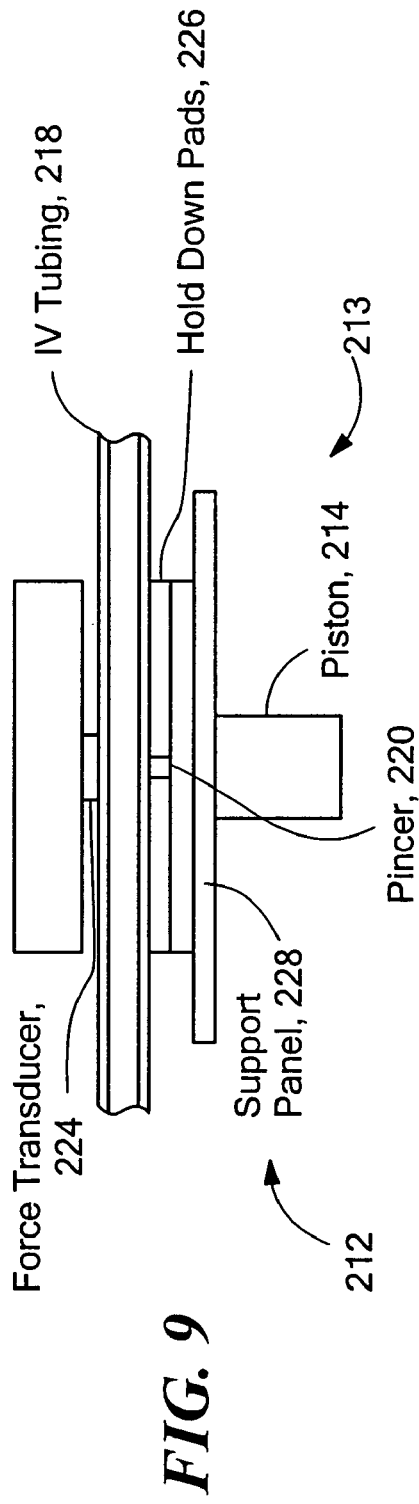
FIG. 9 schematically illustrates a front view of an intravenous (IV) flow control system of the present invention.
Figure 10:
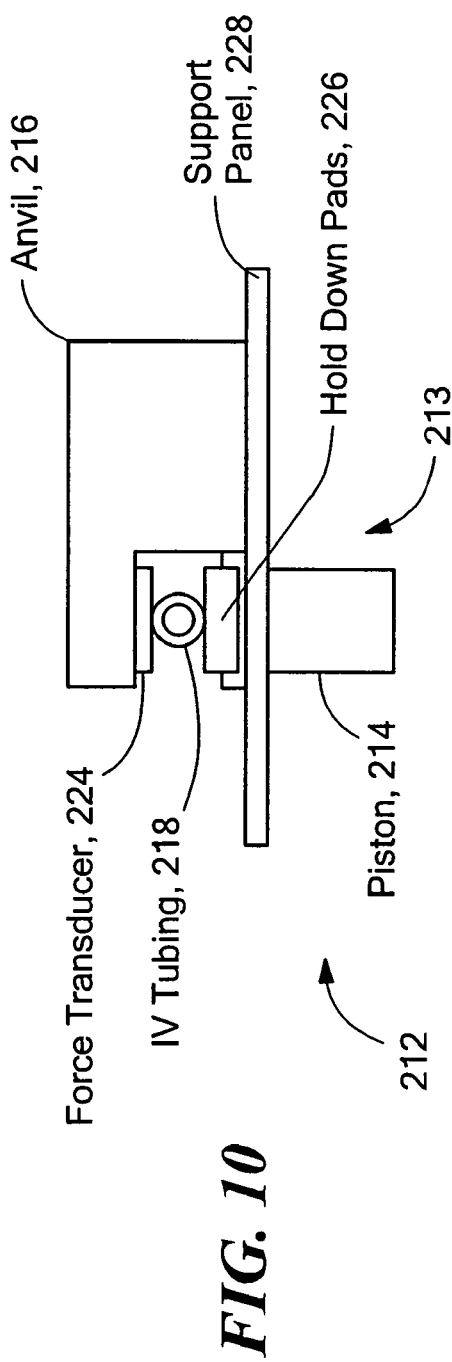
FIG. 10 schematically illustrates a side view of the IV flow control system of FIG. 9.
Figure 11:
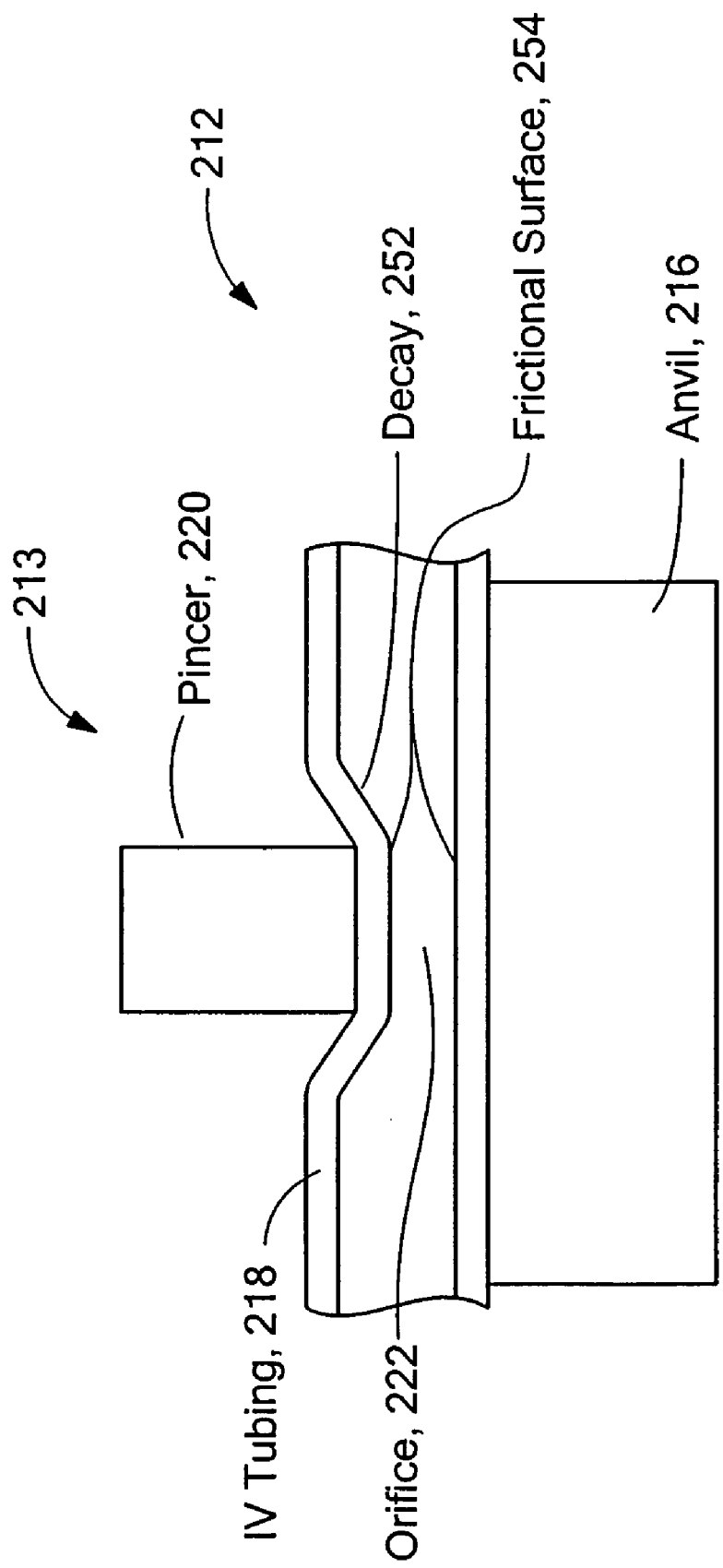
FIG. 11 schematically illustrates the pincer of the IV flow control system of FIG. 9 compressing an IV tubing portion.

Referring to FIGS. 9-11, the flow control system employs a holding or clamping mechanism 212 to retain the tubing in place and a movable element 213 that squeezes or compresses the IV tubing 218. In the embodiment illustrated, the movable element comprises a piston 214 that operates in conjunction with an anvil 216. A pincer 220 of a determined width is disposed at the end of the piston adjacent the tubing to impinge thereon. The anvil is fixed and the piston is driven toward the tubing, thereby squeezing the tubing between the pincer and the anvil. By driving the piston toward and away from the anvil, the tubing at the pincer acts as an orifice 222 to allow more or less fluid flow through the orifice, thereby allowing control of the fluid flow rate. Any suitable mechanism for driving the piston can be employed, such as a linear stepper motor 246 (see FIG. 12). A force transducer 224 mounted between the IV tubing 218 and the anvil 216 provides a determination of the geometry of the tubing during the crushing or squeezing operation, discussed further below. Hold down pads 226, such as of foam rubber, on a support panel 228 keep the tubing in place so that outside motion does not affect the force transducer.

Figure 12:
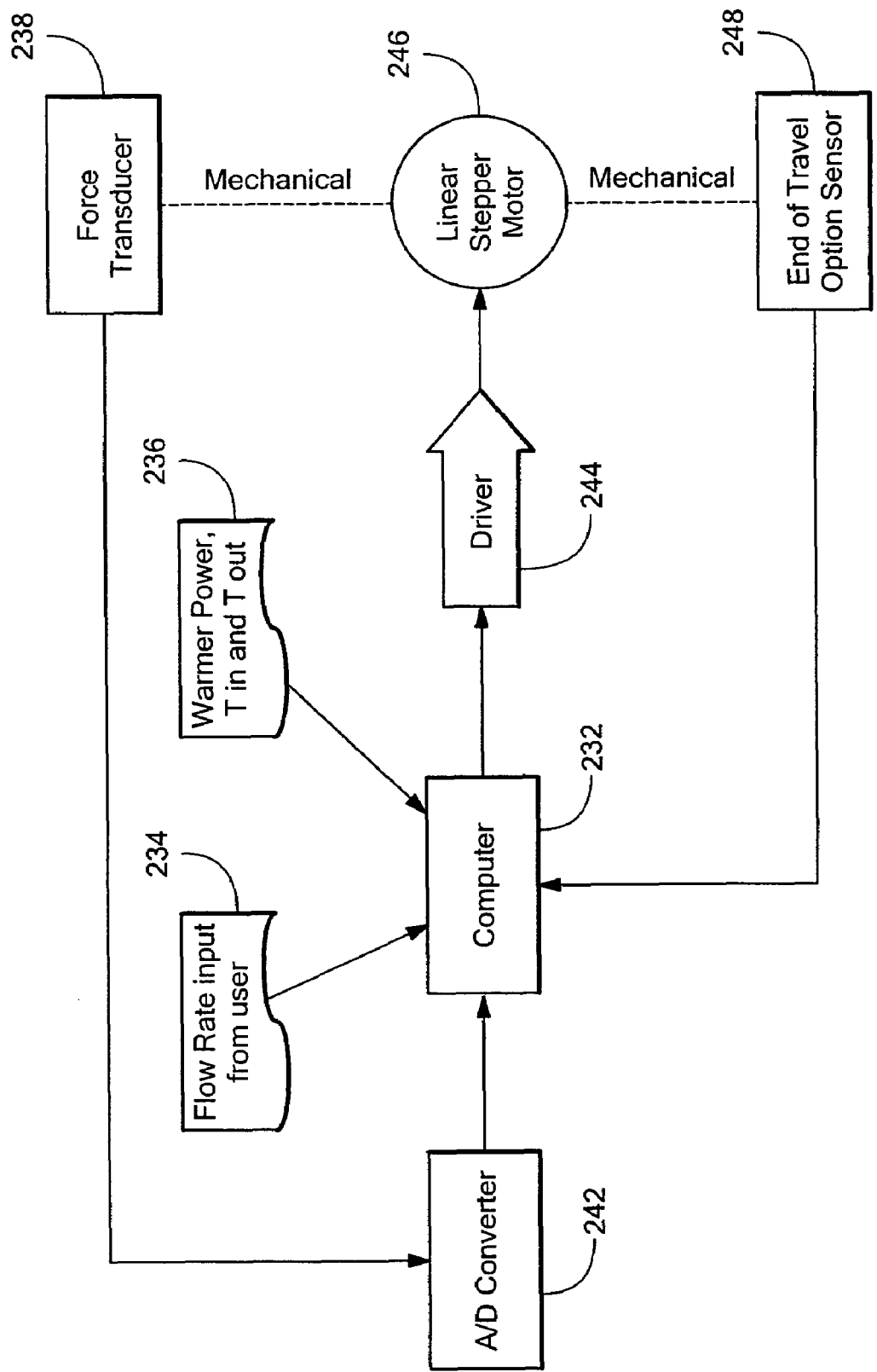
FIG. 12 is a block diagram illustrating control of the IV flow control system.

FIG. 12 further illustrates operation of the IV flow control system. The system includes a computer or controller 232. The desired flow rate 234 is input to the controller by the user. Data 236 from a fluid warmer is also input to the controller for use in the thermally based flow rate calculation. The thermal data includes the power to the fluid warmer, the temperature $T_{in}$ of the IV fluid entering the warmer, and the temperature $T_{out}$ of the IV fluid exiting the warmer. Preferably, the data is automatically transferred from the fluid warmer to the controller. The force transducer 238 provides an indication of the geometry of the tube at the orifice. The signal from the force transducer is transmitted to an A/D converter 242 and then to the controller 232. The controller uses this data for the geometrically based flow rate calculation. The controller determines the actual flow rate at the orifice and then sends a signal via driver 244 to drive the linear stepper motor 246 to advance or retract the piston an appropriate amount to provide an orifice size sufficient to adjust the flow rate to the desired flow rate. A sensor 248 is operative to determine the end of the travel position of the moveable piston to provide a signal indication thereof to the controller.

The controller is able to calculate and control the flow rate using both the thermal and the geometric techniques and can employ one or the other technique as the dominant technique to suit circumstances. When both techniques are used, they can provide a check for each other. Also, the flow rates determined by both techniques can, for example, be averaged to determine a flow rate.

The geometrically based flow rate calculation can be derived as follows. With flow rates normally seen in IV fluid delivery (1 to 20 ml/min), most of the pressure drop occurs across the orifice made by the pincer crushing the tubing. Fluid velocity can be determined from the following relationship:

$$\text{fluid velocity} = \frac{\text{force} \times \text{orifice length}}{\text{frictional surface area} \times \text{viscosity}}$$

The orifice length is the pincer width plus a decay constant due to the slope 252 of the tubing (see FIG. 11). The surface area 254 exposed to the fluid is the orifice length multiplied by π times the inner diameter of the tubing. The force is unknown, but the typical bag height is known, so a rough pressure drop can be calculated:

pressure drop=(fluid density)×g×(bag height above patient)

Figure 13:
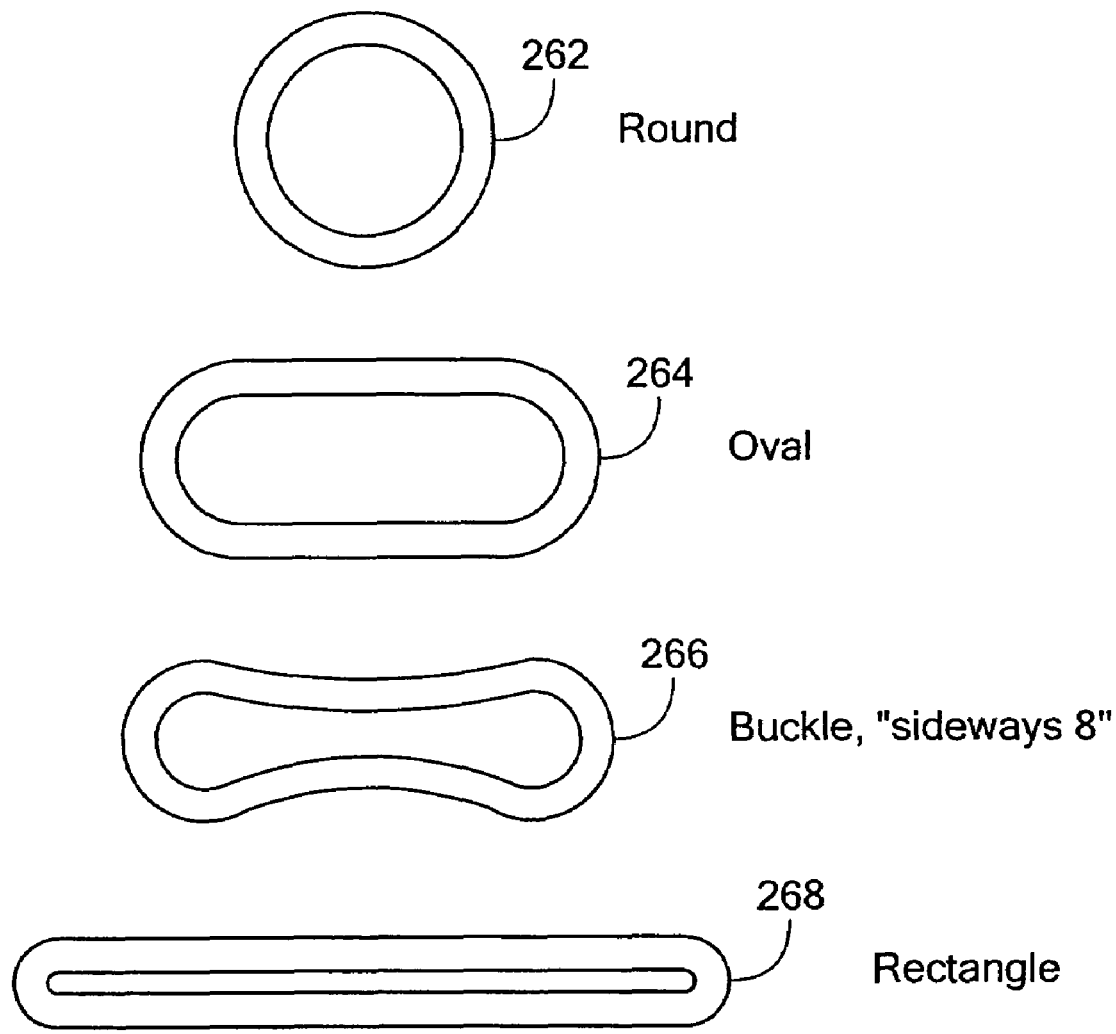
FIG. 13 illustrates cross-sectional geometric configurations of IV tubing at various levels of compression by the IV flow control system of FIG. 9.
Figure 14:
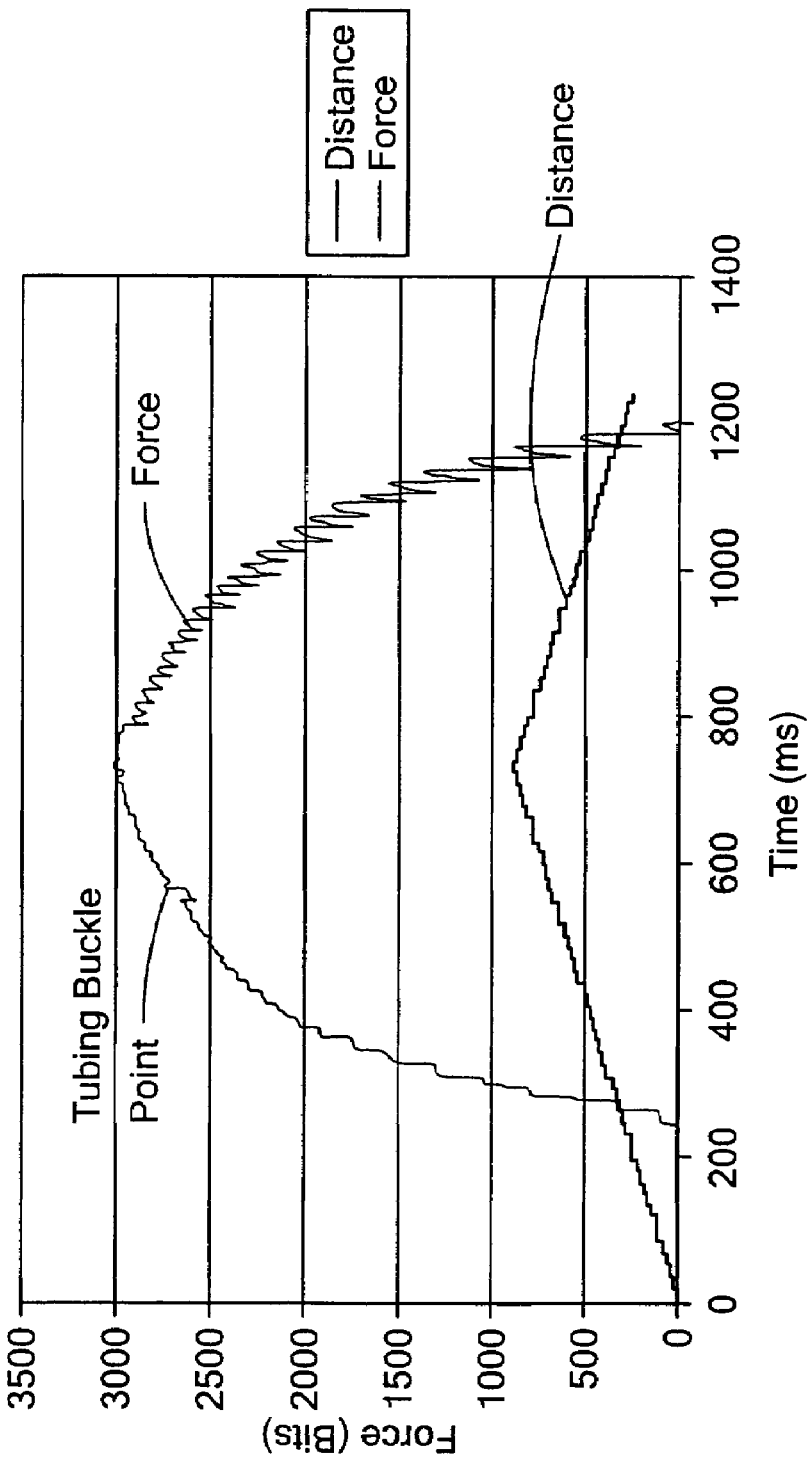
FIG. 14 is a graph illustrating force vs. time at the pincer compressing the tubing.
Figure 15:
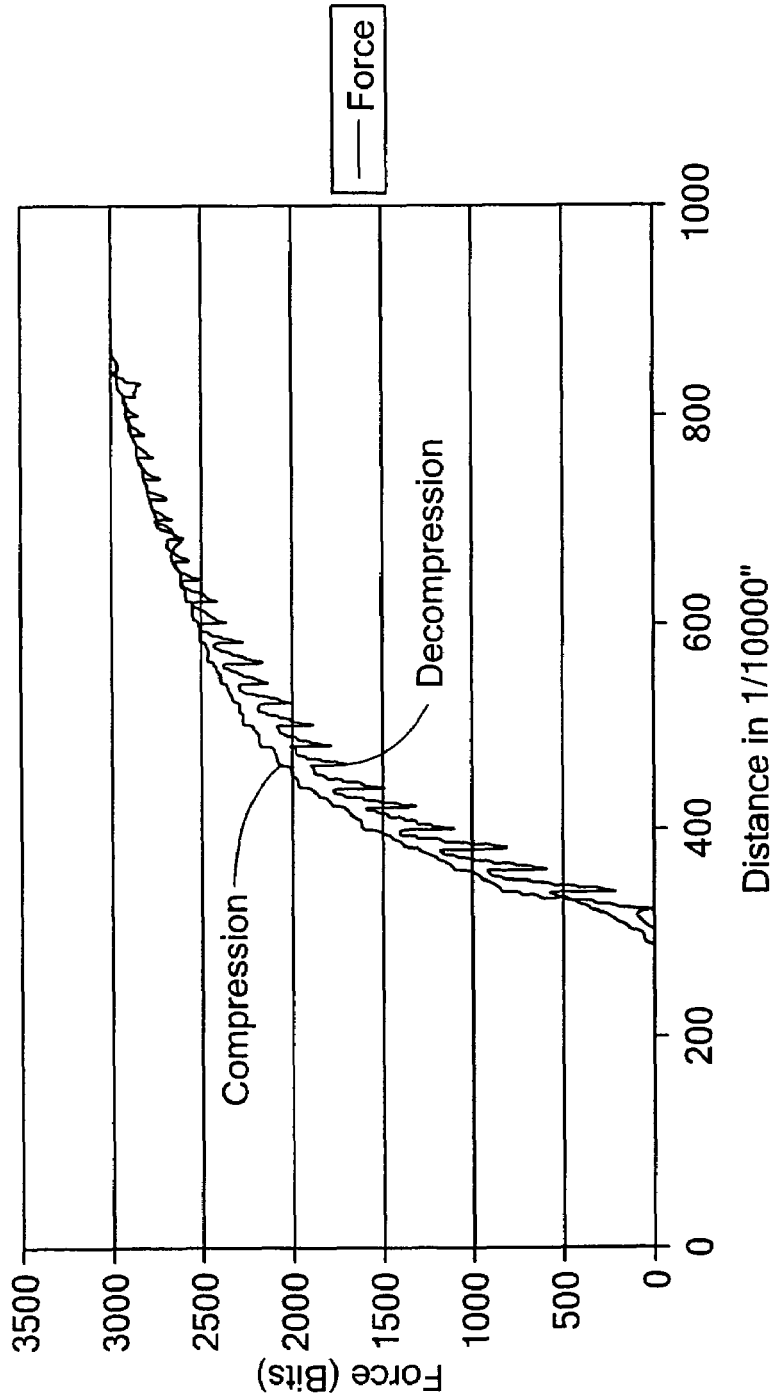
FIG. 15 is a graph illustrating force vs. distance at the pincher compressing the tubing.

If the area of the tubing can be characterized, then the approximate flow rate can be calculated by integrating over the cross sectional area. The main characteristic needed is the cross sectional area through which the fluid flows. When tubing is first inserted in between the anvil and the pincer, the tubing has a round cross-section 262. As the tubing is crushed, its cross sectional area goes from round 262 to oval 264 and then begins to buckle 266, looking like a figure eight, as illustrated in FIG. 13. After the tubing buckles, it takes on more of a rectangular shape 268. The outside diameter, inside diameter, and "buckle" point can be determined by looking at the force transducer and moving the pincer in predetermined steps. These values are determined during calibration at set up when the system is turned on by driving the piston to fully close and then open the tubing and measuring the force at the force transducer at each step that the piston is driven. See FIGS. 14 and 15. Thus, if the dimensions of the tubing are known and the distance from the pincer to the anvil is known, then the cross sectional area can be calculated. The flow rate in a round tube can then be calculated by Poiseulle's law:

$$\text{flow rate} = \frac{\text{pressure drop} \times \pi \left(\frac{\text{orifice diameter}}{2}\right)^4}{\text{viscosity} \times 8 \times \text{orifice length}}$$

In this equation, the orifice diameter and length are known. At low flows, the entire pressure drop can be assumed to be across the orifice, and therefore roughly 65 mm Hg. IV fluids come in two dissimilar physical categories, blood and non-blood solutions. The difference between these fluids is in their viscosity and specific heat. All IV fluids with the exception of blood have a viscosity of 1 cP at room temperature, so the viscosity can be assumed to be 1. Blood has a viscosity varying from 4 cP to 12 cP, depending on flow rate (it is a non-Newtonian fluid) and temperature. By using this method, a rough determination of IV fluid flow rates can be obtained for fluids other than blood. Other standard formulas or derivations can be used for the ovals, buckles and rectangles to obtain the flow rate, as would be known by one of skill in the art. See, for example, Sears, Zemansky, and Young, *University Physics*, Addison-Wesley, 1982, Chapter 13, §§ 13-5, 13-6, "Fluid Dynamics," pp. 271-276.

The largest variable in the geometrically based technique is the pressure, which changes according to bag height, and the second largest variable is the viscosity. These variables are not used in the thermally based technique, which instead utilizes the power input to an IV fluid warmer and the input and output temperatures $T_{in}$ and $T_{out}$ of the IV fluid as the fluid passes through the fluid warmer. Any suitable fluid warming system can be used, such as that disclosed in U.S. patent application Ser. No. 10/876,824, published as U.S. Patent Publication No. US 2005-0008354 A1, incorporated herein by reference.

Using the thermally based technique, the flow rate can be calculated from the following formula:

$$\text{flow rate} = \frac{\text{power}}{\text{density} \times \text{specific heat} \times (T_{out} - T_{in})}$$

In this case, $T_{out}$, $T_{in}$, power, and fluid density are known. $T_{in}$ is the temperature at the heat exchanger entrance at the tubing, and $T_{out}$ is the temperature at the heat exchanger exit at the tubing. The specific heat of the fluid is variable. All IV fluids have a specific heat of 1 cal/gm° C. while whole blood has a specific heat about 0.85 cal/gm° C.

In practice, blood for IV infusions is refrigerated before use. The system can determine whether blood or a standard IV fluid is being used in most cases by looking at $T_{in}$. The system can also determine the fluid type (blood or a standard IV fluid) by calculating the specific heat using the geometrically based technique. If the specific heat does not coincide with the expected constant, then by adjusting the pressure and viscosity variables in the geometric technique and the specific heat in the thermal technique, the approximate actual flow rate can be determined, and the motor can be operated to drive the piston to the correct position to obtain the desired flow rate.

The shape of the tubing can change over time. For example, the tubing can take on a set, or the tubing material can soften if, for example, a warm fluid flows through the tubing. Thus, the controller is operative to continually measure the force from the transducer and servo the motor to maintain the force at the initial or desired value.

At low flow rates, accurate control of the pincer valve can be difficult to achieve. For example, it can be difficult to measure movement of the piston of 0.001 inch or less. In this case, the system is operative to open and close the pincer valve at a duty cycle to obtain average lower flow rates with more accuracy.

In some situations, only one technique may be used, or one technique may be used preferentially over the other. For example, at higher flow rates, at which the orifice pressure drop is not dominant, the thermally based technique above can be used as the dominant technique, and the geometrically based technique can be used to determine whether the IV fluid is or is not blood. In another example, during system start up, the geometrically based technique can be used while the temperatures at the fluid warmer are stabilizing, which can take several minutes.

The system has additional capabilities. The controller is operative to determine the approximate volume of an IV fluid that has been infused by integrating the flow rate over time. If a squeeze bulb infuser is used, the force transducer can detect the large pressure change and provide a signal to the controller to open the pincer valve, thereby allowing the user to give a large volume of fluid in a short period of time. The system can provide a bolus feature by which the user can run the system at an initially high flow rate and then have the system reduce the flow after a specific amount of time has elapsed or a specific volume of fluid has been infused. The valve can clamp the tubing to stop flow in the event of a dangerous condition such as the detection of air in the tubing or an over temperature of the warmer.

Figure 16:
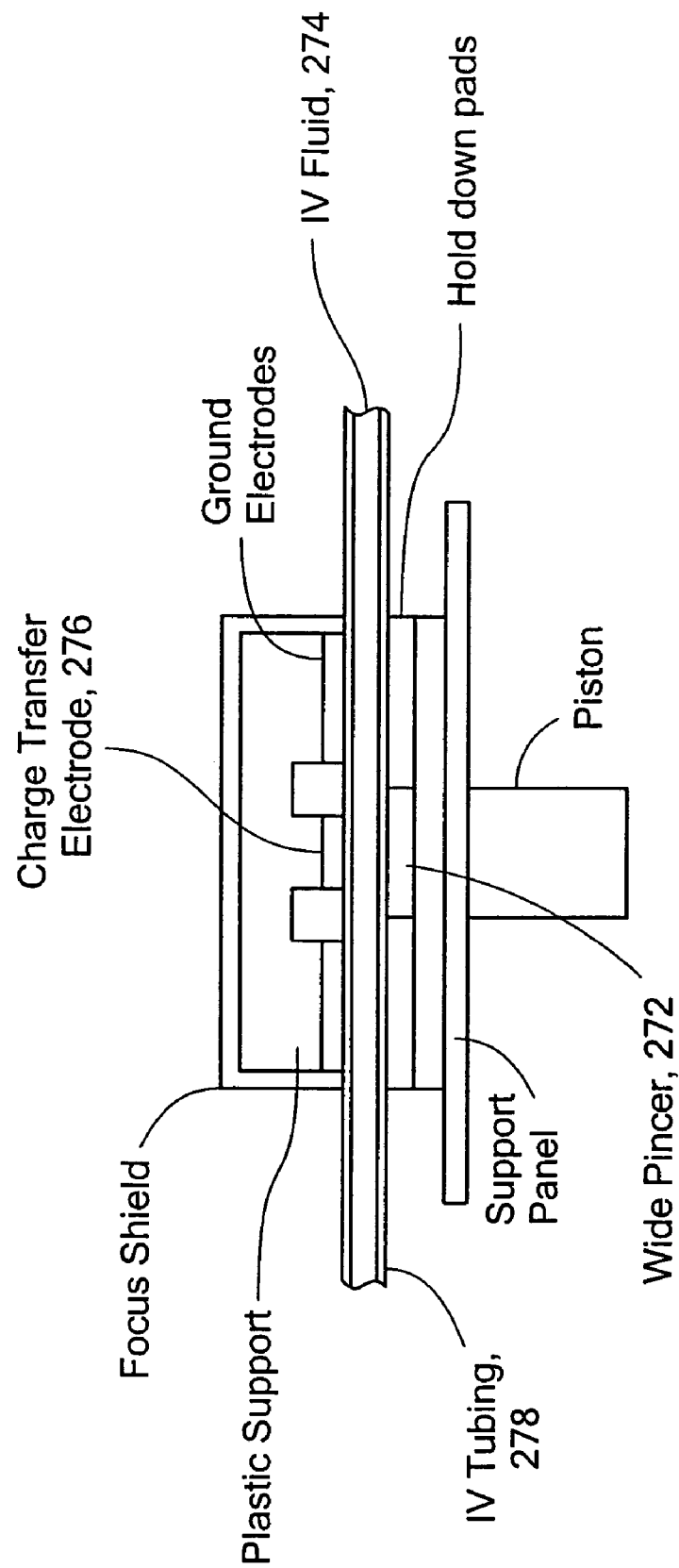
FIG. 16 is a schematic illustration of a further embodiment of a flow control system of the present invention employing a wide pincer and a dielectric tubing detection mechanism.
Figure 17:
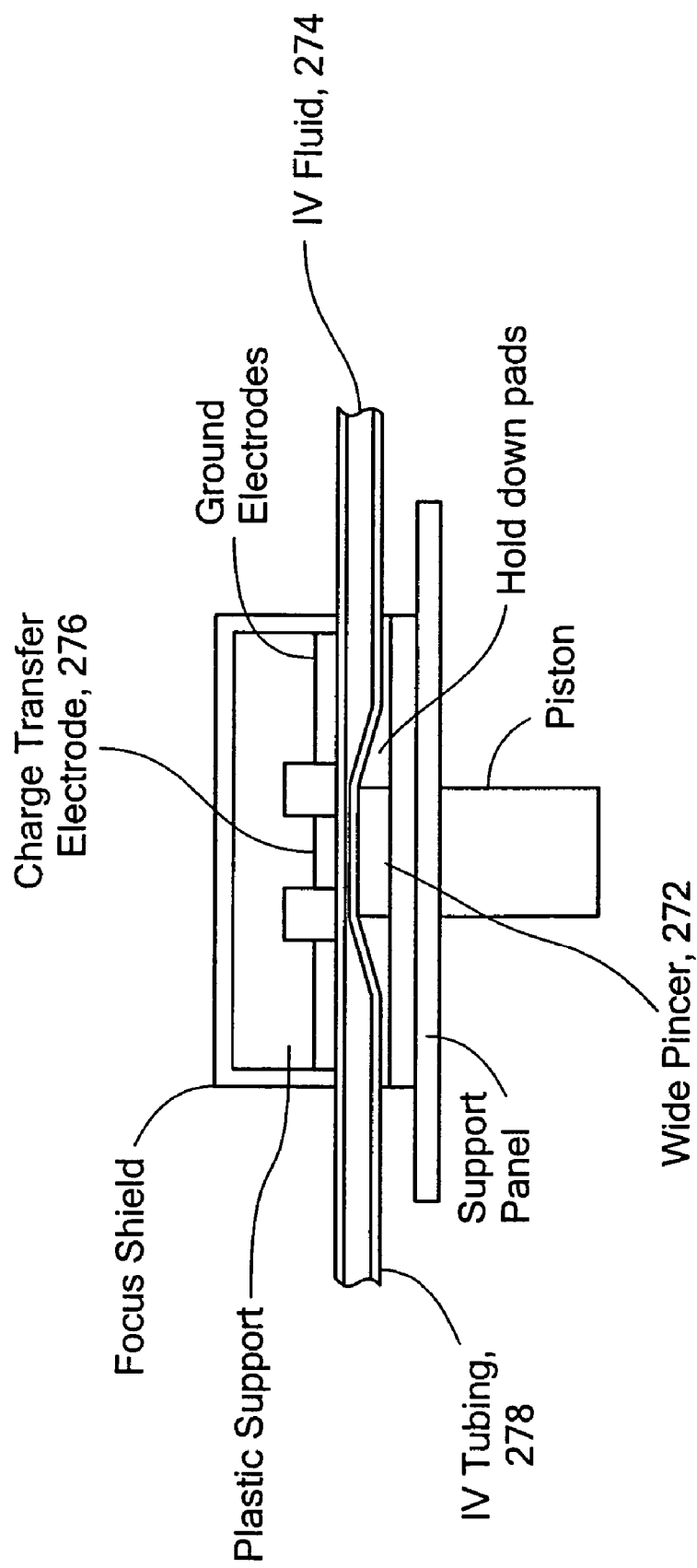
FIG. 17 is a schematic illustration of the wide pincer IV flow control system of FIG. 16 compressing tubing.
Figure 18:
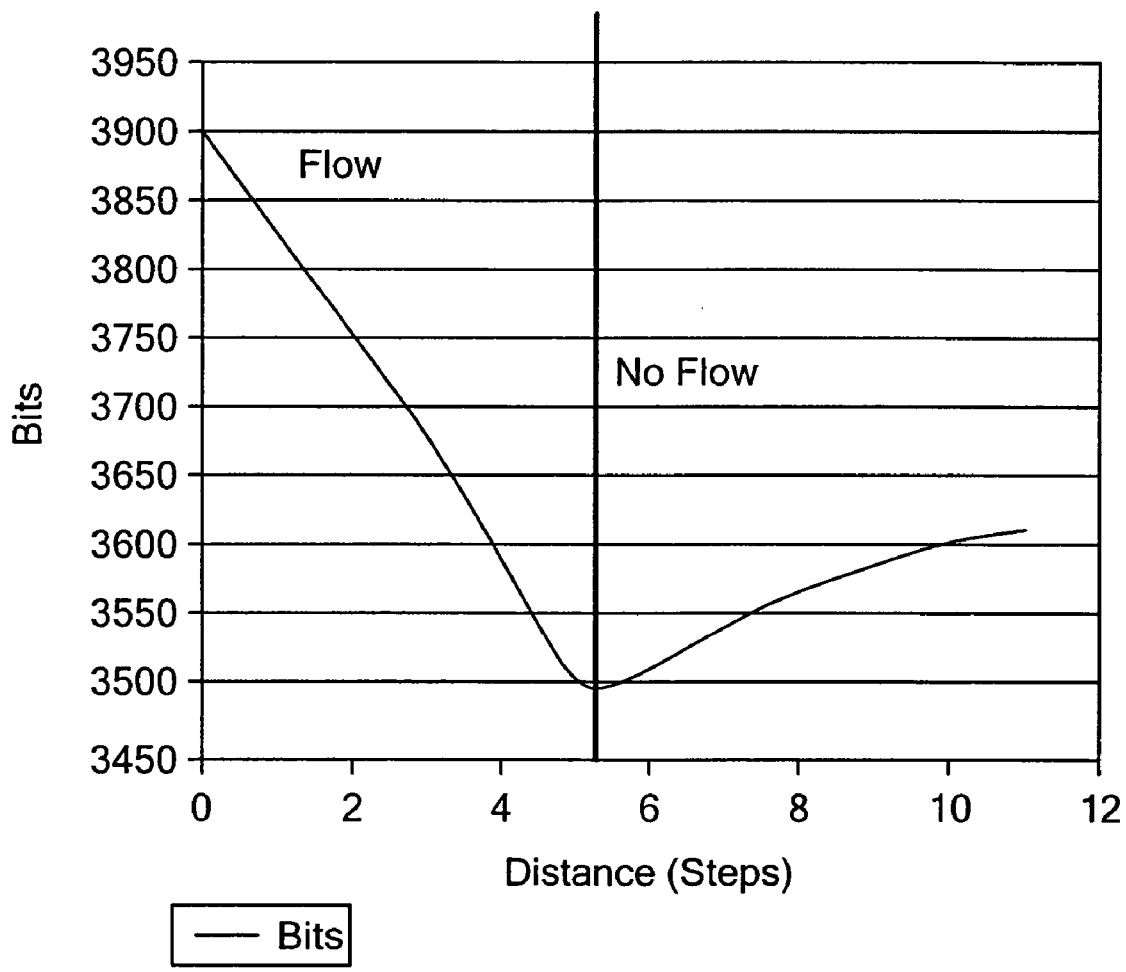
FIG. 18 is a graph illustrating dielectric measurement as a function of crush at full compression.

The IV flow control system can also be used in conjunction with the gas detection system of the present invention described above. In one embodiment, illustrated in FIGS. 16 and 17, if a sufficiently wide pincer is used, the gas detector can detect the dielectric of the tubing to determine if the pincer valve is fully closed, in which case only tubing is present. When closed, the wide pincer 272 displaces all of the fluid 274 to the sides of the sense electrode 276 and the only dielectric left is the tubing 278 and pincer. FIG. 18 shows the dielectric reduction as the IV fluid is displaced until it reaches a minimum value at the point where just the plastic pincer and the tubing remain. The dielectric begins to rise after this point as the tubing is compressed and the pincer gets closer to the sense electrode. In this case, the controller determines that the valve is closed and no fluid is flowing through the orifice. This feature can be used, for example, to provide bolus control or to clamp the tubing closed in case sufficient air is detected to trigger an alarm or if the temperature of the IV fluid exiting the fluid warmer becomes too great.

The system is beneficial for a number of reasons. It uses standard hospital IV sets and standard hospital procedure. It adapts to real time changes in tubing. It handles both standard IV fluids and blood. The operator only needs to set the desired flow rate, greatly simplifying operation. The flow rate is calculated in two independent ways, which overcomes the drawback of using only one or the other technique.

The invention is not to be limited by what has been particularly shown and described, except as indicated by the appended claims.

What is claimed is:

1. A system for the removal of gas bubbles from an intravenous liquid flowing in intravenous tubing, the system comprising:
   a drip chamber having an inlet connected to intravenous tubing from an intravenous source and an outlet connected to intravenous tubing to a patient, the inlet disposed at a higher level than the outlet, wherein the drip chamber retains gas at an upper portion thereof;
   a liquid level sensor operative to sense the level of liquid in the drip chamber;
   a vent valve at an upper portion of the drip chamber operative to open upon a predetermined increase of gas pressure within the drip chamber;
   a continuously operative pump upstream of the drip chamber operative to continuously pump the intravenous liquid from the intravenous source to the patient;
   an occlusion valve downstream of the drip chamber operative to stop liquid flow in the intravenous tubing from the drip chamber to the patient; and
   a controller in communication with the liquid level sensor and the downstream occlusion valve and operative to close the downstream occlusion valve upon detection of a specified liquid level in the drip chamber detected by the liquid level sensor, whereby continued pumping operation of the upstream continuously operative pump while the downstream occlusion valve is closed causes an increase of pressure in the drip chamber sufficient to open the vent valve and release gas in the drip chamber.

2. The system of claim 1, wherein the vent valve comprises a check valve.

3. The system of claim 1, wherein the vent valve comprises an umbrella check valve.

4. The system of claim 1, further comprising a hydrophobic filter disposed before the vent valve to prevent the intravenous fluid passing through the vent valve.

5. The system of claim 1, wherein the controller is further operative to open the occlusion valve.

6. The system of claim 1, wherein the liquid level sensor comprises a variable level sensor to detect a high liquid level and a low liquid level in the drip chamber and the controller is operative to provide an indication of detection of a predetermined high liquid level.

7. The system of claim 1, further comprising a further liquid level sensor operative to detect a high liquid level in the drip chamber and the controller is operative to provide an indication of detection of a predetermined high liquid level.

8. In an intravenous system including a drip chamber having an inlet connected to intravenous tubing from an intravenous source and an outlet connected to intravenous patient tubing, wherein the drip chamber retains gas at an upper portion thereof, and a continuously operative pump upstream of the drip chamber operative to continuously pump intravenous liquid from the intravenous source to the patient, a method for removal of gas in the drip chamber, the method comprising:
   providing a liquid level sensor for sensing liquid level in the drip chamber;
   providing a vent valve at an upper portion of the drip chamber;
   providing a valve downstream of the drip chamber;
   closing the downstream valve in response to a predetermined liquid level sensed by the sensor to cause, by continued operation of the continuously operation pump, an increase in pressure in the drip chamber sufficient to open the vent valve and release gas from the drip chamber; and
   after release of gas from the drip chamber, opening the downstream valve.

9. The method of claim 8, further comprising:
   sensing a low liquid level and a high liquid level in the drip chamber; and
   providing an indication of detection of a predetermined high liquid level.

10. A method for removal of gas from an intravenous fluid line in an intravenous fluid infusion system, comprising:
    providing an intravenous infusion system comprising an intravenous fluid line, a continuously operative pump to deliver intravenous fluid to a patient through the intravenous fluid line, and a drip chamber downstream of the continuously operative pump, a vent valve disposed at an upper portion of the drip chamber;
    continuously pumping the intravenous fluid to a patient through the fluid line;
    collecting intravenous fluid in a bottom portion of the drip chamber prior to infusion to the patient and retaining gas in an upper portion of the drip chamber;
    sensing a liquid level in the drip chamber;
    occluding the fluid line at a location downstream of the drip chamber in response to a predetermined level in the drip chamber sensed by the sensor sufficient to cause an increase in pressure in the drip chamber by continued pumping operation of the continuously operative pump to open the vent valve and release gas from the drip chamber; and
    after release of gas from the drip chamber, opening the fluid line to allow fluid flow to resume through the fluid line.

11. The method of claim 10, further comprising sensing a low liquid level and a high liquid level in the drip chamber; and
   providing an indication of detection of a predetermined high liquid level.

* * * * *